United States Patent [19]

Schwan

[11] 4,018,823
[45] Apr. 19, 1977

[54] 4',5'-DIMETHOXY-2',3-DIAMINOPROPI-OPHENONE DIHYDROCHLORIDE

[75] Inventor: Thomas J. Schwan, Norwich, N.Y.

[73] Assignee: Morton-Norwich Products, Inc., Norwich, N.Y.

[22] Filed: Apr. 20, 1976

[21] Appl. No.: 678,531

[52] U.S. Cl. .................. 260/570.5 C; 260/592; 424/330
[51] Int. Cl.² ........................................ C07C 97/10
[58] Field of Search ..................... 260/570.5 C

[56] References Cited

UNITED STATES PATENTS 3,236,892  2/1966  Petrocek .................. 260/570.6

Primary Examiner—Robert V. Hines
Attorney, Agent, or Firm—Anthony J. Franze

[57] ABSTRACT

4',5'-Dimethoxy-2',3-diaminopropiophenone dihydrochloride possesses pharmacological activity as a hypotensive agent.

1 Claim, No Drawings

4',5'-DIMETHOXY-2',3-DIAMINOPROPIOPHENONE DIHYDROCHLORIDE

This invention relates to a compound of the formula:

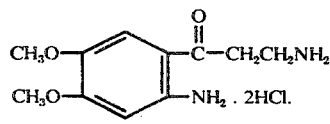

When administered intravenously to animals this compound exhibits hypotensive activity. Intravenous administration of 50 mg/kg of this compound dissolved in physiologically acceptable menstrua to anesthetized dogs resulted in blood pressure lowering for about 5 hours.

In order that this invention be readily available to and understood by those skilled in the art, the following illustrative example is included: A. 3',4'-Dimethoxy-3-nitropropiophenone. Aluminum chloride (173 g, 1.30 moles) was added quickly to 700 ml vigorously stirred nitrobenzene. While the temperature was maintained between 10° and 15° there was added a solution of 91 g (0.59 mole) of β-nitropropionyl chloride in 50 ml nitrobenzene followed by a solution of 73 g (0.53 mole) veratrole in 50 ml nitrobenzene. The mixture was stirred at room temperature for 6 hours and then poured cautiously into a mixture of 300 ml concentrated HCl and 2 kg iced water. The organic layer was separated and the aqueous material was extracted with 3 × 200-ml portions of chloroform. The combined organic layers were washed with 300 ml water, 300 ml 10% sodium carbonate, and 2 × 300-ml portions of water. After the solution was dried over magnesium sulfate, the solvents were removed in vacuo to give the oily product. Cystallization from ethyl acetate gave 45.5 g (36%) of A, m.p. 113-118°. An analytical sample m.p. 126-128°, was obtained by recrystallization from ethanol.

Anal. Calcd for $C_{11}H_{13}NO_5$: C, 5.48; N, 5.86 Found: C, 55.11; H, 5.78; N, 5.59 B. 4',5'-Dimethoxy-2',3-dinitropropiophenone. To 300 ml concentrated nitric acid stirred and maintained at 5-10° was added over 20 minutes in small portions 45.5 g (0.19 mole) of A. The resulting solution was stirred at 5° for 10 minutes and then added slowly to 2.5 kg iced water. The suspension was stirred at room temperature for 20 minutes and filtered. The solid was washed with 3 × 200-ml portions of water, air dried, and dried at 60° to give 48 g of crude B, m.p. 120-127°. Recrystallization from 2 l. ethanol gave 34 g (63%) of B, m.p. 135-140°. An analytical sample, m.p. 140-142°, was obtained by recrystallization from alcohol.

Anal. Calcd for $C_{11}H_{12}N_2O_7$: C, 46.48 H, 4.26; N, 9.86 Found: C, 46.62; H, 4.39; N, 9.78 C. 4',5'-Dimethoxy-2',3-diaminopropiophenone dihydrochloride A 17.3 g (0.61 mole) portion of B, 500 ml methanol, 240 ml methanol saturated with HCl, and 22 g 5% Pd/C (50% moisture) was shaken on a Parr apparatus at room temperature until the theoretical quantity of hydrogen was consumed (5.5 hours). The catalyst was filtered and the resulting solution was concentrated to dryness at 35—45° in vacuo. The residue was slurried with ethanol and the solid was filtered to give 13.5 g of the crude product, m.p. 204°-209°.

The material was recrystallized from ethanol and the solid was washed with 70 ml ethanol to afford 5.3 g (29%) of the product, m.p. 208-214°.

An analytical sample, m.p. 202-207°, was recrystallized from ethanol containing HCl.

Anal. Calcd for $C_{11}H_{18}N_2O_3 \cdot 2HCl$: C, 44.45; H, 6.10; N, 9.43 Found: C, 44,63; H, 6.35; N, 9.21

What is claimed is:

1. The compound of the formula:

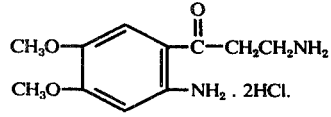

* * * * *